United States Patent [19]

Groh et al.

[11] 4,144,454

[45] Mar. 13, 1979

[54] TAPE TRANSPORT MECHANISM

[75] Inventors: Edward F. Groh, Naperville; William McDowell, Downers Grove; Norbert S. Modjeski, Oak Lawn; Donald J. Keefe, Lemont, all of Ill.; Peter Groer, Knoxville, Tenn.

[73] Assignee: The United States of America as represented by the United States Department of Energy, Washington, D.C.

[21] Appl. No.: 763,164

[22] Filed: Jan. 27, 1977

[51] Int. Cl.² .................. G01N 21/30; B65H 25/04; B65H 25/32
[52] U.S. Cl. .................. 250/435; 242/75.5; 242/190; 242/201; 242/206; 250/571
[58] Field of Search ............ 242/182, 183, 184, 185, 242/189, 190, 201, 67.2, 75.5, 206; 250/435, 571

[56] References Cited

U.S. PATENT DOCUMENTS

| 2,814,676 | 11/1957 | House | 242/190 |
|---|---|---|---|
| 2,952,010 | 9/1960 | Demer et al. | 242/185 |
| 2,972,678 | 2/1961 | Anton | 250/435 |
| 3,109,096 | 10/1963 | Spaa | 250/435 |
| 3,937,421 | 2/1976 | Fender et al. | 242/182 |

Primary Examiner—George F. Mautz
Attorney, Agent, or Firm—Dean E. Carlson; Frank H. Jackson; Paul A. Gottlieb

[57] ABSTRACT

A device is provided for transporting, in a stepwise manner, tape between a feed reel and takeup reel. An indexer moves across the normal path of the tape displacing it while the tape on the takeup reel side of the indexer is braked. After displacement, the takeup reel takes up the displaced tape while the tape on the feed reel side of the indexer is braked, providing stepwise tape transport in precise intervals determined by the amount of displacement caused by the indexer.

12 Claims, 5 Drawing Figures

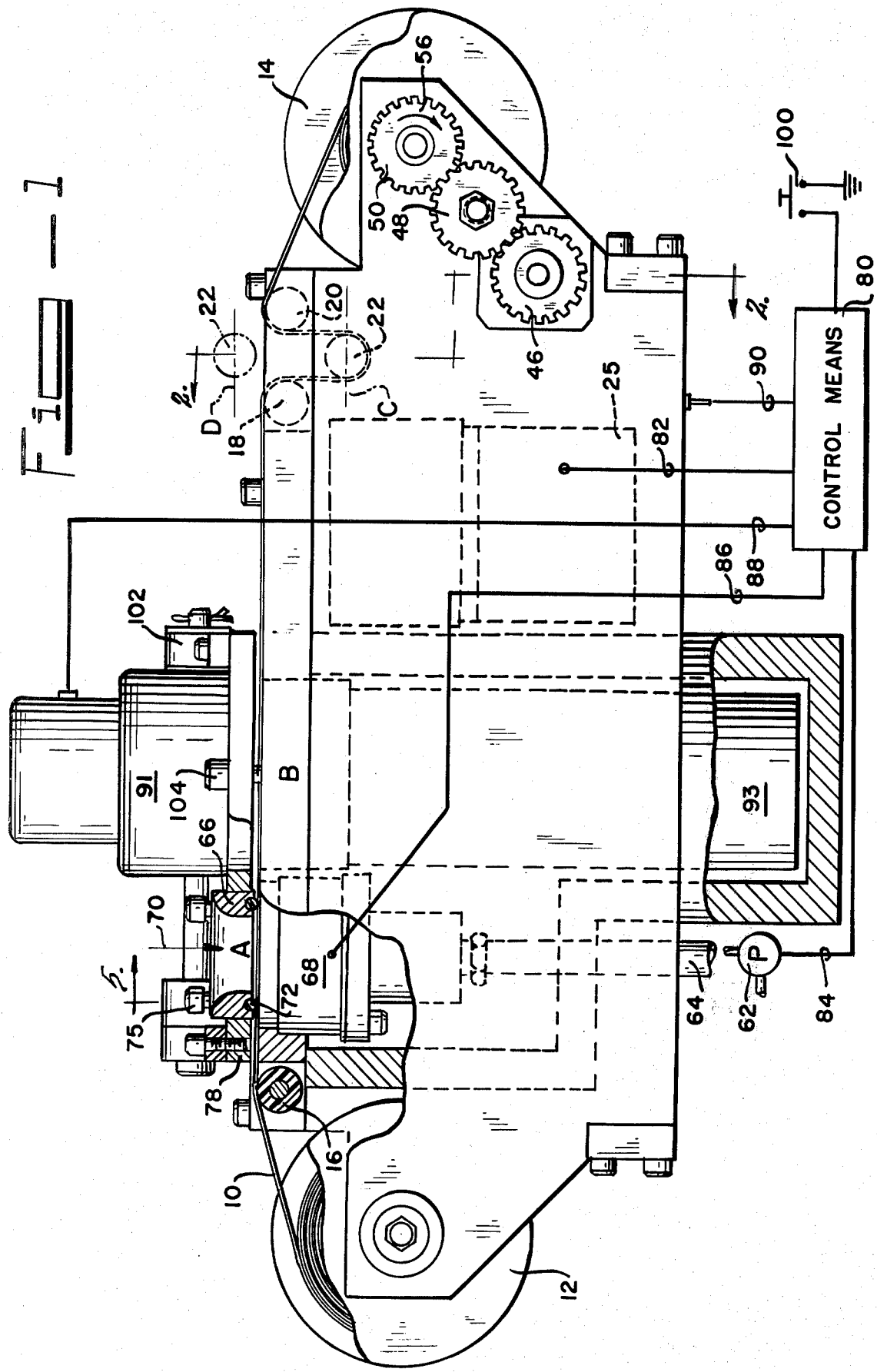

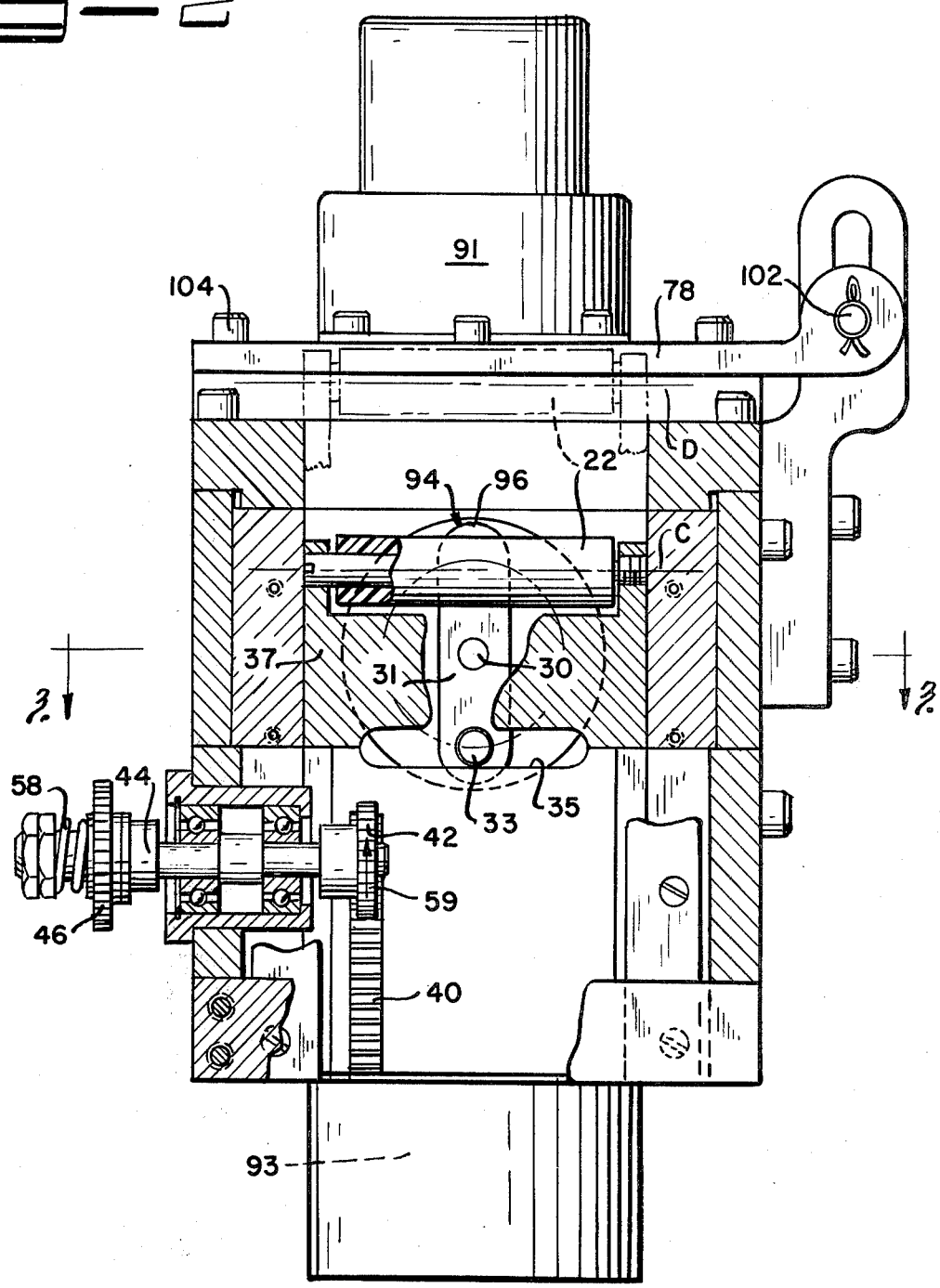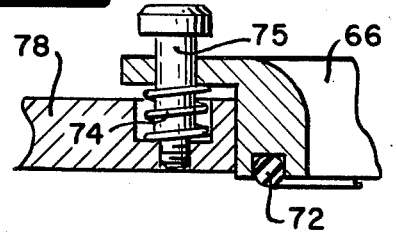

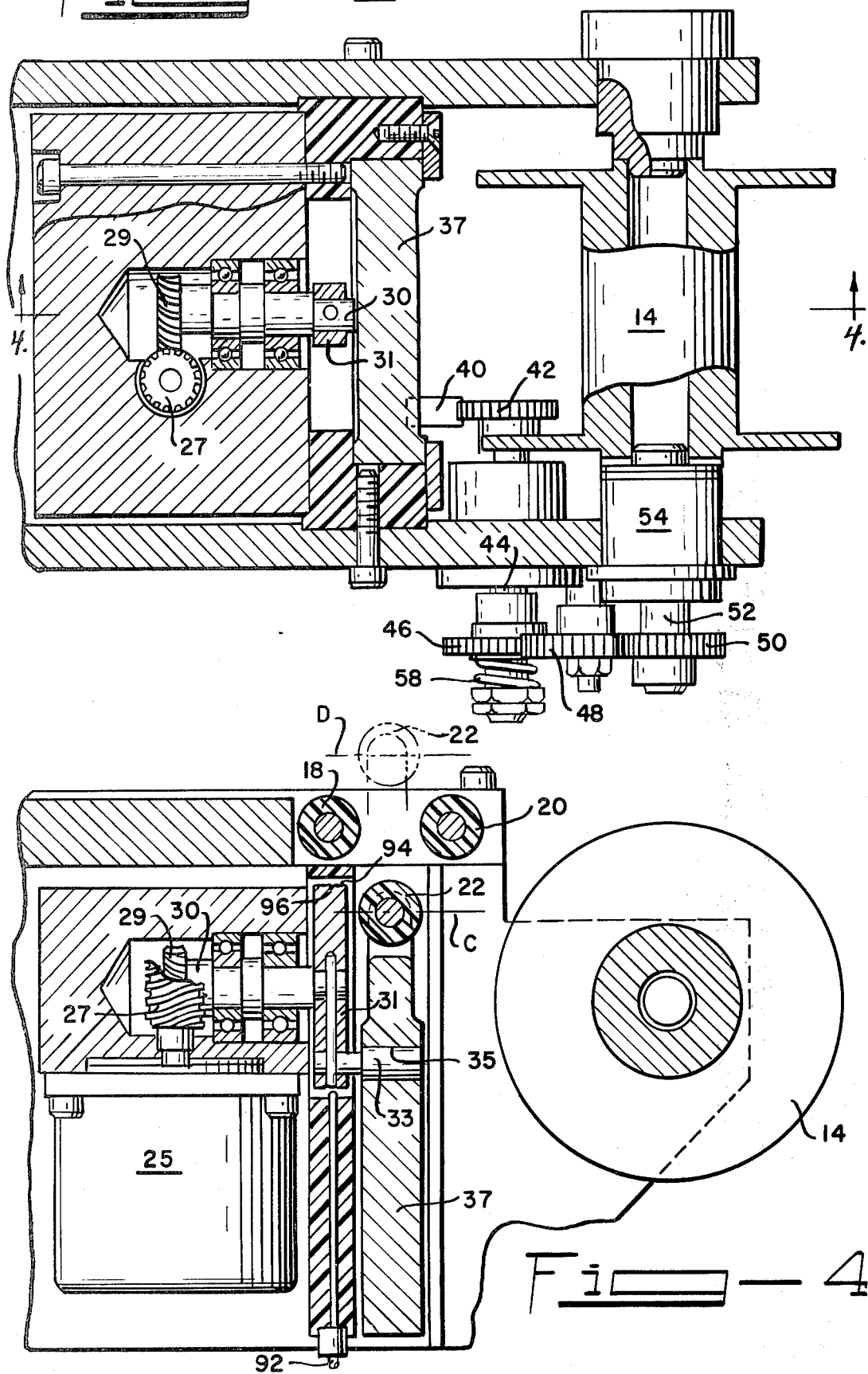

TAPE TRANSPORT MECHANISM

CONTRACTUAL ORIGIN OF THE INVENTION

The invention described herein was made in the course of, or under, a contract with the United States Energy Research and Development Administration.

BACKGROUND OF THE INVENTION

Many types of scientific monitors utilize a tape or piece of paper to record or gather the monitored information. For example, in a remote working level meter, such as described in U.S. Pat. No. 3,555,278 of Schroeder entitled "Potential Alpha Ray Activity Meter," a test sample is collected by exposing a portion of porous tape to a volume of air. Detection means are then utilized to determine from the tape whether particular elements are present. Manual handling, in such a device, may be minimized by providing it with a tape transport mechanism. In such devices, the exposure of the tape, normally a porous filter paper, is done by pumping a known flow rate of air through a fixed area of the tape for a fixed time period at one station and then transporting the tape with the tape transport mechanism to another station where detection is undertaken. The transport mechanism handles a supply of tape so that a plurality of monitoring events can be obtained without the necessity of continually changing the tape for each monitoring event.

To insure the proper accuracy of the measurements obtained from such a portable monitor, it is necessary that the transporting of the tape between stations be in a precise manner so that the entire area of the tape that has collected the desired sample is repeatedly positioned in a precise geometry with respect to the detector. Prior art stepwise tape transport mechanisms include tape perforated at precise intervals with the intervals detected such as by a photoelectric cell. For certain types of tough plastic tape, perforating is difficult. Another stepwise transport mechanism is an indexed takeup reel which takes up a precise interval of tape. An indexed takeup reel, however, has a higher degree of inaccuracy than may be desirable.

It is therefore an object of this invention to provide a mechanism for transporting a tape between two or more stations.

Another object of this invention is to provide such a tape transport mechanism wherein movement of the tape is in a precise stepwise fashion.

SUMMARY OF THE INVENTION

A device is provided for transporting a tape in a stepwise manner along a particular path between a feed reel and a takeup reel. The device includes an indexer and means for oscillating the indexer so that the indexer oscillates between a position of minimum and maximum displacement of the tape from its normal path. As the indexer is moving from the minimum to the maximum position, the tape is braked on the takeup reel side of the indexer and while the indexer is moving from the maximum to the minimum position, the tape is braked on the feed reel side of the indexer. The takeup reel is activated, and thereby collects the precise amount of tape displaced by the indexer as the indexer moved from the minimum to the maximum position. Control means are coupled to the indexer to control the precise displacement and to activate appropriate detection and sampling means at each station between which the tape is transported. The amount of displacement in each cycle is predetermined to correspond to the distance between each station.

BRIEF DESCRIPTION OF THE DRAWINGS

FIG. 1 is a partial cross section of a particular monitor utilizing the tape transport mechanism herein disclosed;

FIG. 2 is a cross section through line 2—2 of FIG. 1;

FIG. 3 is a cross section through line 3—3 of FIG. 2;

FIG. 4 is a cross section through line 4—4 of FIG. 3; and

FIG. 5 is a cross section of the sealing means at station A of FIG. 1.

DETAILED DESCRIPTION OF THE INVENTION

Referring to FIGS. 1-5, there is shown a remote working level monitor incorporating a particular tape transport mechanism. Tape 10 is transported between feed reel 12 and takeup reel 14 in a stepwise manner. The tape may be any flexible narrow band of material capable of being rolled between a feed reel and a takeup reel. In the embodiment shown, at station A, a precise area of tape 10 is exposed to a volume of air. The precise area of tape 10 is then transported to station B where an analysis is undertaken, such as with a scintillation counter. To insure precise stepwise movement of the tape between stations A and B and to provide for continuous operation of the monitor, a particular tape transport mechanism is provided. The path traveled by tape 10 is defined by fixed guide rollers 16, 18 and 20. For the precise stepwise movement of tape 10, an index roller 22 is utilized to displace tape 10 from its normal path defined by the fixed guide rollers 16, 18 and 20 while tape 10 is braked on the takeup reel side of index roller 22. Thus unrolling of tape 10 from feed reel 12 will occur. The tape 10 is then braked on the feed reel side of index roller 22 and then, while the index roller 22 is moved to a position where it does not displace tape 10, takeup reel 14 is made to take up the precise amount of tape displaced by roller 22.

In particular, a motor 25 is provided which drives a shaft 27 which in turn drives a worm gear 29. Worm gear 29 is coupled via shaft 30 to crank 31. Crank 31 has on one end a pin 33 which extends into slot 35 of indexer 37. Mounted on indexer 37 is the index roller 22. The combination of shaft 30, crank 31, pin 33, slot 35, and indexer 37 forms a Scotch yoke assembly, whereby rotational motion of the shaft 30 is translated into linear motion of the indexer 37. Indexer 37 will oscillate back and forth between two positions as the shaft 30 completes one revolution. This is shown in FIG. 2 where index roller 22, as shown in the heavy lines, is at position C which corresponds to maximum deflection of tape 10 from its normal path by roller 22 and in phantom at the minimum position D of the least displacement of tape 10 by roller 22. Thus, when roller 22 is traveling from position D to position C, force will be exerted on tape 10 to displace it from its normal path as shown in FIG. 1 while, when roller 22 is traveling from position C to position D, no force is transmitted to tape 10 by roller 22, tending to displace tape 10 from its normal path. By braking the tape and advancing the takeup reel at appropriate times, this action of roller 22 on tape 10 can be utilized for precise stepwise advancement of tape 10.

Indexer 37 is provided with a geared rack 40 which moves up and down as indexer 37 moves up and down. Rack 40 engages gear 42 mounted on shaft 44. At the other end of shaft 44 is gear 46 which drives gear 48 which drives gear 50. Gear 50 is at the end of shaft 52 of takeup reel 14. Shaft 52 is provided with a one-way clutch bearing 54 which permits rotation of shaft 52 and thus reel 14 only in the clockwise direction shown by arrow 56. A slip clutch 58 on shaft 44 allows the driving force imparted to gear 42 by rack 40 to be communicated to gear 46 only when that force will turn gear 50 in the direction of arrow 56 and disengages shaft 44 from communication with gear 46 when one-way bearing 54 prevents motion of gear 50 in the direction opposite of arrow 56.

As index roller 22 travels from D to C, rack 40 will turn gear 44 in the direction of arrow 59 which, when communicated by shaft 44, gear 46 and gear 48 to gear 50, would tend to turn gear 50 in a direction opposite arrow 56. This would be prevented by one-way bearing 54 and therefore slip clutch 58 will disengage shaft 44 from communicating force to gear 46. The effect of this action is to brake reel 14 so that during traveling of index roller 22 from D to C, tape 10 can only be supplied to the displaced path by feed reel 12.

On the opposite stroke of indexer 37, the rotation of gear 42 by rack 40 will be in the proper direction to drive gear 50 in the direction of arrow 56 and clutch 58 will engage shaft 44 with gear 46. Assuming tape 10 is braked on the feed reel side of index roller 22, the rotation of reel 14 as roller 22 moves from C to D will take up the precise amount of excess tape displaced when roller 10 moved from D to C and no more. Braking of tape 10 on the feed reel side of roller 22 can be done by appropriate clutching of reel 12 or by a clamping of tape 10. The amount of rotation of reel 14 to take up a given length of tape 10 will decrease as the diameter of the tape on reel 14 increases. The gearing (gears 46, 48 and 50) are chosen so that the greatest rotation of reel 14 will be at the smallest diameter of tape on reel 14. As the diameter of reel 14 increases, the clamp on tape 10 provided by block 66, as will be described, and the action of slip clutch 58, prevents reel 14 from rotating after the disposed tape has been wound.

In the figures the monitor shown is a remote working level monitor. In the operation of such a device, air is pumped through tape 10 at station A by a pump 62 coupled to hose 64. To insure accurate results, it is necessary that the air be pumped through a precise area of tape 10. This is accomplished by sealing block 66 and solenoid 68. At the appropriate time, as will be described later, block 66 which is of a magnetic material is attracted by solenoid 68 in the direction of arrow 70. As shown in FIG. 5, block 66, which includes a magnetic material which defines the desired area of paper and a ring seal 72, is mounted on frame 78 and biased by a spring 74 on each screw 75 away from tape 10. With activation of solenoid 68, seal 72 defines and seals the precise area of tape 10 and will also effectively clamp tape 10 so that, when takeup reel 14 is winding displaced tape, only the exact amount of displaced tape is actually wound.

The actual operation of the meter is controlled by control means 80. Control means 80 is basically a logic device which controls activation of motor 25, solenoid 68, pump 62 and whatever detection equipment is present at station B. To facilitate such control, motor 25 is preferably a stepping motor. Control means 25 is coupled to motor 25 by lead 82. Control means 25 includes a pulse source which applies pulses to motor 25 thereby activating motor 25. Control means 80 is coupled to pump 62 by lead 84, to solenoid 68 by lead 86, and to detectors at station B by lead 88. It also applies appropriate signals to these devices to activate them.

Control means 80 monitors the position of tape 10 by means of lead 90 which supplies information from proximity sensor 92. Proximity sensor 92 is intended to detect the position of crank 31. When crank 31 is in a position which corresponds to index roller 22 being at position D, this information is supplied to control means 80. This may be accomplished by providing that the outer circumferential surface 94 of crank 31 is black except for a single scribe 96 at the end of crank 31 opposite the end of pin 33. Light emitted by sensor 92 will not be reflected back to sensor 92 by the black portions of crank 31 but, when the crank 31 is at the minimum position, light will be reflected by scribe 96 and detected by sensor 92. This will then be sent via pulse to control means 80, indicating that index roller 22 is at position D corresponding to minimum deflection of tape 10.

The operation of the working level monitor utilizing the particular tape transport mechanism is activated such as by having a button 100 pushed. Control means 80 responds to switch 100 being pushed by zeroing crank 31. Pulses are sent via lead 82 to motor 25, thereby activating motor 25 until sensor 92 indicates that roller 22 is at position D. Normally this will be the condition of the monitor before button 100 is pushed. At this point control means 80 sends a predetermined number of pulses to motor 25 which coincides exactly with one revolution of crank 31 or one cycle of roller 22 between positions D and C. As has previously been described, while roller 22 is traveling from D to C, takeup reel 14 is braked by one-way bearing 54, solenoid 68 is inactivated, seal block 66 is raised above tape 10, and roller 22 displaces a precise predetermined amount of tape 10. After exactly one-half of the predetermined number of pulses has been applied to motor 25, which corresponds to roller 22 being at position C, solenoid 68 is activated by control means 80. As roller 22 then travels from C to D, reel 14 is driven by motor 25 via indexer 37 and rack 40, and reel 14 takes up the displaced tape with seal 72 of block 66 acting as a clamp on tape 10 so only the amount of tape actually displaced is taken up by reel 14.

At this point, the area of tape originally at station A when button 100 was pushed will be at station B and a new area of tape at station A. The area originally at A is ignored since it may be contaminated from having sat at A while the machine was not being used. If the background count of the background level of the tape without air being drawn through it is desired, then control means 80 may repeat the cycle and move the second area of tape to station B and activate the detectors there, to take such a reading. Either after the background count, if any, is taken or after the first move to position a clean area of paper at station A, control means 80 activates pump 62 (solenoid 68 remains activated after the completion of the original cycles until the end of the pumping cycle. The precise volume of air is drawn by pump 62 through the area of paper at station A. After this has occurred, the motor is activated for a complete cycle, thereby moving the exposed tape to position B where control means 80 activates the detectors. Detectors 91 and 93 may be located both above and below tape 10 at station B and might, for example, be scintillation counters.

The amount of tape displaced is determined by the penetration of index roller 22 into the normal path of tape 10, which in turn is controlled by the radius of crank 31. To vary the amount of a particular application, one needs only provide means for varying the radius described by pin 33. This could be done by providing a slot in the center of crank 31 to allow adjustment. An alternate method of varying the penetration of index roller 22 would be to vary the location of points C and D with respect to tape 10 by providing means for varying the height where roller 22 starts above tape 10. Replacement of tape is further facilitated by providing that all the elements surrounding tape 10, namely those at station A and station B of frame 78, are mounted on a hinge 102 and by releasing screw 104, the whole mechanism may be pivoted about the hinge and the tape may be replaced on the rollers in the normal manner for such tape replacement.

Of course, the tape transport mechanism is usable with any kind of device requiring stepwise tape transport. Thus filter paper, such as would be used in a working level meter, may be utilized with the tape transport mechanism.

The advantages of the disclosed tape transport mechanism are the precision obtainable for repeatedly moving a given length of tape, and the gentle treatment of the tape by the transport mechanism. The gentle treatment arises because the sinusoidal motion of index roller 22 applies a gradually increasing and then decreasing force on tape 10 rather than a sudden jerk as a constant force mechanism would apply. The device has been described as one with two stations, A and B, at which the tape is acted upon. More than two stations may be utilized provided the control means 80 is properly configured and programmed.

The embodiments of the invention in which an exclusive property or privilege is claimed are defined as follows:

1. A device for transporting a tape in a stepwise manner along a particular path between a feed reel and a takeup reel, comprising:

an indexer, oscillator means coupled to said indexer for oscillating said indexer linearly between a maximum and minimum point wherein at said maximum point said indexer displaces the tape from said particular path a maximum amount and at said minimum point said indexer displaces said tape from said particular path a minimum amount, forward brake means capable upon activation of preventing the tape from moving between the feed reel and said indexer in the direction from said feed reel to said takeup reel, reverse brake means capable upon activation of preventing the tape from moving between the takeup reel and said indexer in the direction from said takeup reel to said feed reel, control means coupled to said indexer and said forward and reverse brake means such that with said indexer moving from said minimum to said maximum point, said control means activates said reverse brake means, and such that with said indexer moving from said maximum to said minimim point said control means activates said forward brake means, and forward drive means coupled to said takeup reel for taking up displaced tape with said forward brake activated, said forward drive means including a rack gear mounted on said indexer and moving together therewith in said linear oscillating motion, and gearing so engaged with the takeup reel and said rack gear that with said indexer moving from said maximum to said minimum point said rack gear drives said gearing which drives the takeup reel in a direction so that the tape displaced by said indexer is collected by said takeup reel.

2. The device of claim 1 wherein said gearing includes slip clutch means such that with the tape being prevented from moving in the direction from the takeup reel to the feed reel said clip clutch means prevents said rack gear from driving said takeup reel.

3. The device of claim 2 wherein said forward brake means includes a block of magnetic material, and a solenoid, both positioned between said feed reel and said indexer, the particular path along which the tape is transported lying between said block and said solenoid, said solenoid being coupled to said control means such that with activation of said solenoid by said control means said block is attracted to said solenoid, thereby clamping the tape therebetween, the clamping of the tape by said solenoid and said block being with sufficient force that said slip clutch prevents said rack gear from driving said takeup reel after tape displaced by said indexer has been collected on said takeup reel.

4. The device of claim 3 wherein said oscillator means includes a Scotch yoke assembly coupled to said indexer.

5. The device of claim 4 wherein said Scotch yoke assembly includes a stepping motor as the source of rotational motion thereof, said control means activating said motor and thereby said oscillator means by applying pulses to said motor.

6. The device of claim 5 further including a sensor coupled to said control means for indicating the position of said indexer, said control means being responsive to said sensor indicating that said indexer is at said minimum point to apply a predetermined number of pulses to said motor to inactivate said solenoid, and to activate said reverse brake means, with one-half of said predetermined number of pulses applied to said motor said control means inactivating said reverse brake means and activating said solenoid.

7. The device of claim 6 wherein said reverse brake means includes a one-way bearing upon which the takeup reel is mounted, said bearing permitting rotation of the takeup reel only in the direction which will tend to move the tape from said feed reel to said takeup reel, said bearing being thereby activated to prevent the tape from moving from said takeup reel to said feed reel with said indexer moving from said minimum to said maximum point, as such motion of said indexer will tend to rotate said takeup reel opposite to the direction 10 permitting by said one-way bearing.

8. The device of claim 7 wherein along the particular path of the tape are a plurality of stations at which the tape is to be acted upon, at each station there being an apparatus coupled to said control means, said control means being responsive to the sensor indicating the position of the tape to control activation of each apparatus.

9. The device of claim 8 wherein said device is part of an air monitoring system and said solenoid and block are at a first station of said plurality of stations, said block having a hole therethrough so that with the tape clamped thereby a particular area of the tape is exposed through said hole, and further including means for drawing air through said hole onto the tape at said first station, said means for drawing being coupled to said control means and being activated thereby.

10. The device of claim 9 wherein said block includes a sealing ring positioned about said hole corresponding to said particular area so that with clamping of the tape by said block and solenoid said particular area is sealed and precisely defined.

11. The device of claim 10 wherein there is a second station positioned between said first station and said takeup reel and at which there is at least one detector coupled to said control means, said control means being capable of activating said detectors, said second station being positioned a distance from said first station equal to a multiple of the length of tape defined by said particular area so that said means for transporting can be activated by said control means, the particular area of the tape exposed during said activation of said means for drawing can be transported to said second station by said control means activating said motor, and said detectors can be activated by said control means with said particular area exposed at said second station.

12. The device of claim 11 wherein the particular path is defined by a plurality of fixed rollers in contact with the tape, and said indexer has mounted thereon an index roller which is made to contact and displace tape during oscillation of said indexer.

* * * * *